(12) United States Patent
Davis et al.

(10) Patent No.: US 7,622,134 B2
(45) Date of Patent: Nov. 24, 2009

(54) SUBSTRATE FOR VOLATILE DELIVERY SYSTEMS

(75) Inventors: Brian T. Davis, Burlington, WI (US); Robert R. Emmrich, Racine, WI (US); Michael J. Aulozzi, Racine, WI (US); Padma Prabodh Varanasi, Racine, WI (US); Michael C. Fryan, Racine, WI (US); Kenneth J. Welch, Racine, WI (US); Stanley J. Flashinski, Racine, WI (US); Debra A. Strasser, Franksville, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 798 days.

(21) Appl. No.: 11/255,479

(22) Filed: Oct. 21, 2005

(65) Prior Publication Data

US 2006/0039945 A1 Feb. 23, 2006

Related U.S. Application Data

(62) Division of application No. 10/354,876, filed on Jan. 30, 2003, now Pat. No. 7,138,130.

(51) Int. Cl.
*A01N 25/08* (2006.01)
(52) U.S. Cl. ............... 424/421; 43/129; 424/40; 424/417; 424/764; 424/DIG. 10; 514/65; 514/521; 514/522; 514/531; 514/919
(58) Field of Classification Search ............... None
See application file for complete search history.

(56) References Cited

U.S. PATENT DOCUMENTS

| 100,327 | A | * | 3/1870 | Robbins ............ 514/731 |
| 3,166,615 | A | | 1/1965 | Farrell |
| 3,652,197 | A | | 3/1972 | Tokarz |

(Continued)

FOREIGN PATENT DOCUMENTS

EP 841070 A2 5/1998

(Continued)

OTHER PUBLICATIONS

Material Safety Data Sheet for Resin Coated Silica Sand from Fairmount Minerals, Oct. 26, 1998.

(Continued)

*Primary Examiner*—Neil Levy

(57) ABSTRACT

Volatile impregnated substrates, such as wicks and mats, that can be used in a dispensing device that uses a heat source or otherwise uses active means to promote the release of the volatile material from the substrate are disclosed. The preferred substrate has a structure including sand particles adhered together by a binder to form a network of pores and passages. The binder is selected from thermoset polymeric materials and mixtures thereof. A volatile material is disposed in the pores before the substrate is installed in the dispensing device. The impregnated substrate is positioned in the dispensing device on or near the heat source of the dispensing device. The heat source is activated thereby elevating the temperature of the substrate such that volatile material is released from the pores. In one embodiment, the sand particles comprise silica sand and the binder is a cured novolac resin.

15 Claims, 7 Drawing Sheets

U.S. PATENT DOCUMENTS

| | | | |
|---|---|---|---|
| 4,286,754 A | 9/1981 | Jones | |
| 4,391,781 A | 7/1983 | van Lit | |
| 4,439,415 A | 3/1984 | Hennart et al. | |
| 4,627,963 A | 12/1986 | Olson | |
| 4,663,315 A | 5/1987 | Hasegawa et al. | |
| 4,849,181 A | 7/1989 | Kelley et al. | |
| 4,968,487 A | 11/1990 | Yamamoto et al. | |
| 5,038,394 A | 8/1991 | Hasegawa et al. | |
| 5,095,647 A | 3/1992 | Zobele et al. | |
| 5,222,186 A | 6/1993 | Schimanski et al. | |
| 5,290,546 A | 3/1994 | Hasegawa et al. | |
| 5,547,616 A | 8/1996 | Dancs et al. | |
| 5,647,053 A | 7/1997 | Schroeder et al. | |
| 5,807,539 A * | 9/1998 | Tsukii et al. | 424/40 |
| 5,945,094 A | 8/1999 | Martin et al. | |
| 5,981,622 A | 11/1999 | Geoffrey | |
| 6,031,967 A | 2/2000 | Flashinski et al. | |
| 6,078,728 A * | 6/2000 | O'Rourke et al. | 392/390 |
| 6,210,625 B1 * | 4/2001 | Matsushita et al. | 264/610 |
| 6,309,986 B1 | 10/2001 | Flashinski et al. | |
| 6,361,752 B1 | 3/2002 | Demarest et al. | |
| 6,446,384 B2 | 9/2002 | Pedrotti et al. | |
| 6,482,365 B1 | 11/2002 | Soller | |

FOREIGN PATENT DOCUMENTS

| | | |
|---|---|---|
| GB | 2289409 A | 11/1995 |
| GB | 2327349 A | 1/1999 |
| WO | WO 00/78135 A2 | 12/2000 |
| WO | WO 01/02025 A1 | 1/2001 |

OTHER PUBLICATIONS

Material Safety Data Sheet for Resin Coated Chromite Sand from Fairmount Minerals, Oct. 29, 1998.

Material Safety Data Sheet for Resin Coated Zircore Sand from Fairmount Minerals, Oct. 29, 1998.

Material Safety Data Sheet for Resin Coated Zircon Sand from Fairmount Minerals, Oct. 29, 1998.

* cited by examiner

SUBSTRATE FOR VOLATILE DELIVERY SYSTEMS

CROSS-REFERENCES TO RELATED APPLICATIONS

This is a divisional application of U.S. application Ser. No. 10/354,876 filed Jan. 30, 2003 now U.S. Pat. No. 7,138,130.

STATEMENT REGARDING FEDERALLY SPONSORED RESEARCH

Not Applicable.

BACKGROUND OF THE INVENTION

1. Field of the Invention

This invention relates to volatile dispensing devices that employ active means to dispense volatiles from a volatile-impregnated substrate. More particularly, the invention relates to improved volatile impregnated substrates, such as wicks and mats, that can be used in a volatile dispensing device that employs active means to dispense.

2. Description of the Related Art

The following definitions apply herein: An "effective amount" or an "effective delivery rate" and the like term is defined to mean that amount or rate sufficient to achieve the intended effect. "Active means" is defined as heat, moving air, or other means of imparting energy to a volatile material to be dispensed, and a volatile dispensing device that employs active means to dispense volatiles will be referred to as "actively dispensing" the volatile material. To be effective, insect control volatile active ingredients have to be delivered at no less than an "insect controlling rate," defined herein as that rate sufficient to repel or otherwise control target insects within the space to be protected.

Devices for dispensing thermally or otherwise volatilizable materials into the atmosphere are well known. Such volatilizable materials may be air scents (e.g. fragrances), pest control materials (e.g., insecticides), allergen control ingredients, disinfectants, and the like.

In one type of volatile material dispensing device, a heat source is used to promote the wicking action and release of a volatile material from a wick, one end of which is immersed in a volatile liquid contained in a reservoir. One version of this type of device is plugged into an electrical wall outlet to supply power to a heating coil within a housing. The generated heat raises the temperature of a material contained in the wick and volatilizes the material. Convection air currents dispense the volatilized material into the room. Examples of this type of device and related devices can be found in U.S. Pat. Nos. 6,361,752; 5,647,053; 5,290,546; 5,222,186; 5,095,647; 5,038,394; and 4,663,315. The disclosure of these patents and all other publications referred to herein are incorporated herein by reference as if fully set forth.

In another type of volatile material dispensing device, a stiff, porous mat (commonly made of a pressed, cellulosic, fibrous material) is impregnated with a volatile material, or a volatile material is placed in a pan-like metal structure. These mats and pans are then placed on heaters to cause the volatile material to vaporize into the atmosphere. One type of heater used for this purpose is sold by S. C. Johnson & Son, Inc. under the trademark "FUYI VAPE". Examples of this type of device and related devices can be found in U.S. Pat. Nos. 6,446,384; 6,309,986; 6,031,967; 5,945,094; and 4,391,781.

In yet another type of volatile material dispensing device, a stiff, porous mat is impregnated with a volatile material, and the mat is held within the device such that a flow of hot gases from a fuel burner passes over the mat and causes the volatile material to vaporize into the atmosphere. An example of this type of device can be found in PCT International Patent Publication No. WO 00/78135.

In yet another type of volatile material dispensing device, moving air is directed against a substrate or through a reticulated or otherwise airflow-transmitting substrate to thereby volatilize volatile material with the substrate has been impregnated. Examples of this type of device can be found in U.S. Pat. No. 5,547,616 and in PCT International Patent Publication No. WO 01/02025.

While all of these devices provide satisfactory results under certain circumstances, there are drawbacks to each type of device.

In devices that use a heat source to promote the release of a volatile material from a wick immersed in a volatile liquid composed of solvents and dissolved active ingredients, presently available wicking materials limit the performance of the wick of the device. For instance, when using porous wicks made of felt or fabric in such a device, there is a tendency as the wick is heated for the solvents to quickly volatilize off, thereby leaving high boiling point materials behind in the wick. The high boiling point materials remaining in the wick can cause clogging of the wick. Other wick materials include ceramics and compressed sawdust. However, these wicks experience the same sort of clogging when used in a device that uses a heat source to promote the release of a volatile material from a wick immersed in a volatile liquid. As a result, it is difficult to maintain stable evaporation of the volatile liquid for extended time periods. While uniform release of volatiles has been reported in U.S. Pat. No. 4,286,754 for non-heated wicks, the problem of non-linear release in heated wicks remains.

Certain volatile materials, such as some insecticide formulations, include materials that either are or become non-volatile when the liquid is heated in a wick. These non-volatile materials can cause clogging of the wick, which leads to a less uniform release rate of the volatile during use over time and to high residual levels of non-volatile materials in an expended wick. For example, pyrethrum insecticides typically include or form non-volatile waxes or polymers. During use in a dispenser having a conventional ceramic or sawdust wick, these waxes form sludges that can clog the wick. Thus, ceramic and sawdust wick systems do not allow effective utilization of insecticidal formulas that contain natural pyrethrins and terpenes.

One proposed solution to the problems associated with the clogging of wicks by non-volatiles formed by oxidation of pyrethrum insecticides has been the use of antioxidants in the liquid formulation. See, for example, U.S. Pat. No. 4,968,487. However, in spite of antioxidants, some cross-linking of the isoprene units in insecticidal liquid formulations occurs, forming non-volatile components that degrade the wicking performance of traditional wicks. The performance losses in these systems can be attributed to clogging of the small pores and the effects of the high tortuosity (twists and turns) in conventional wick materials.

Certain disadvantages are also seen with devices that use a heat source to promote the release of a volatile material from a solid or stiff porous mat impregnated with a volatile material or of a volatile material placed in a pan-like metal structure. One problem with the metal pan-like structures is that typical heaters can cause a volatile material to be exposed to too much heat. This can cause the volatile to be used up too fast or be deteriorated or destroyed through thermal degradation. Fibrous mats have similar but somewhat lesser problems in this regard.

Dispensing devices using heated mats also have problems with respect to the mats being exposed to differing temperatures across a heater surface. Existing heaters often have hotter regions at certain points along their heater surface, typically generally along a center line. The mats therefore can have uneven and incomplete vaporization. Uneven mat heating can cause the overall rate at which insect control volatile active ingredients are delivered to drop below the insect controlling rate for the active while considerable quantities of the active remain in poorly heated portions of the mat. Indeed, even aside from the issue of uneven heating, mats tend not to deliver a linear release of volatile materials. Commonly, the initial volatile delivery rate is comparatively high, as active accessibly near the surface of the mat quickly volatilizes. Once that accessible active is gone, migration of active from the interior of the mat to the surface can be slow, at least in part because of small, entrapping pores and very convoluted flow paths. The delivery rate decreases until the mat no longer delivers active at an insect controlling rate and must be replaced. It is not uncommon that conventional insecticide mats for use with conventional heaters have released only about 60% of their load of volatile material before the delivery rate falls below an effective, insect controlling delivery rate. This results in waste and therefore in increased cost for such mat products.

Another design consideration for insect control mats is that existing heaters often only accept slab-like inserts having a small cross-sectional shape, necessary to fit into a small heater loading port or opening. Thus, any mat design preferably takes into account size restrictions imposed by existing heaters. Yet another critical design consideration in this type of device is cost. Mats of this type are often used in countries that have very modest average annual incomes. To have much practical application in those countries, the mats must be inexpensive.

Thus, there is a need for an improved liquid-delivery wick that can be used in a dispensing device that uses a heat source or other active means to promote the release of a volatile material from the wick. Furthermore, there is a need for an improved porous mat that can be used in a dispensing device that uses a heat source or other active means to promote the release of a volatile material from the mat. In particular, there is a need for wicks and porous mats that provide improved efficacy (including but not limited to non-clogging, linear, and complete volatile release) and low cost, together with compatibility with existing dispensing devices.

BRIEF SUMMARY OF THE INVENTION

The foregoing needs are met by a substrate made according to the invention for use in a volatile dispensing device that actively dispenses volatile material from the substrate. The substrate includes granular particles adhered together to form a body having a network of pores and passages, the interior surfaces of which are non-reactive and non-absorptive with respect to the volatile material to be dispensed. The term "granular particles" is defined as meaning discrete, monolithic, compact particles (as distinct from linearly extended particles such as fiber strands or substantially continuous, porous materials such as ceramics) that, when packed in a confined space, have points of contact with neighboring particles but also leave open spaces between the particles. Sand particles are an example of such granular particles and are preferred both for their low cost, ability to withstand heat, and non-reactivity. However, glass, high density polymeric particles, and other particles are also possible. Preferred high density polymers are high density polycarbonate and polyethylene polymers. If the granular particles are non-organic, they can be adhered by any convenient means, including but not limited to point fusing by application of heat and/or pressure and/or the use of a polymerizing or other binder, coating, or the like that simply sticks the particles together, the latter means being preferred generally. However, if the granular particles are made of an organic material, the substrate of the invention is limited to particles adhered only by the use of a polymerizing or other binder, coating, or the like, without the use of any sintering step. "Point fusing" is defined as fusing only at points of contact between neighboring particles without a substantial change in the size and shape of the particles or the size and shape of the network of passages and pores left between the particles.

A volatile material is disposed in the pores and passages. Activation of the volatile dispensing device releases the volatile material from the pores and passages, which volatile material is then dispensed. The volatile material may comprise an insect control active ingredient initially deliverable by the dispenser at an insect controlling rate, and preferably no more than 10% residual volatile material remains in the pores when the dispenser has so depleted the volatile material as to no longer be able to deliver the volatile material at the insect controlling rate. When the substrate is used in an insecticide dispensing device, the volatile material is preferably selected from natural pyrethrins, pyrethrum extract, synthetic pyrethroids, and mixtures thereof. When the substrate is used in an air treating dispensing device, the volatile material can be a fragrance or other volatile air treatment material.

In another aspect of the invention, a substrate for a dispensing device that employs active means to promote release of a volatile material from the substrate includes a body including granular particles adhered together by a binder to form a network of pores and passages. The binder is selected from cross-linked polymeric materials and mixtures thereof. In one preferred embodiment, the granular particles are sand particles (and, even more preferred, sand particles that include silica sand), and the binder is a cured phenolic resin such as novolac resin, which is commercially available from many sources. A volatile material is disposed in the pores, thereby impregnating the substrate, preferably before the substrate is installed in the dispensing device but also, optionally, after the substrate is located in or forms a permanent part of a device. In an example embodiment, the volatile dispensing device has a slot through which the substrate can be inserted to load the substrate into the volatile dispensing device, and the substrate is formed into a shape suitable for being suspended in the slot.

The substrate of the invention is positioned in the dispensing device so as to be subjected to the active means for dispensing volatile materials. For example, for a dispensing device that uses heat as that active means, the substrate is positioned on or near the heat source of the dispensing device. In such a device, the heat source is activated, thereby elevating the temperature of the substrate such that volatile material is released from the pores. In a device employing air flow as the active means, the substrate is so placed as to be exposed to the air flow.

In a preferred substrate of the invention, the pores occupy at least 25% percent by volume of the substrate. It is also preferred that the pores have an average size in the range of 20 to 200 microns.

When using a substrate according to the invention in a heated volatile dispensing device, the volatile material is released from the pores at a substantially linear rate until release at an effective rate is no longer achieved. For example, if the volatile material is an insect control active such as transfluthrin, the volatile material is released substantially linearly at an insect controlling rate until an end point is reached, after which very little volatile material remains. Advantageously, as little as 10% residual volatile material remains in the pores after effective release of the volatile material from the substrate ceases, as evaluated and quantified by conventional gas chromatography and mass spectrometric methods. Even more preferred, no more than 5% residual volatile material remains in the pores after effective release of the volatile material from the substrate ceases, as evaluated and quantified by conventional gas chromatography and mass spectrometric methods.

When using a substrate according to the invention, many active ingredients can be used directly to impregnate the substrate, without having to dilute the active ingredients with a solvent. For example, an insect control mat of conventional size (approximately 3.5 by 2 cm.) can be dosed with transfluthrin by depositing the desired amount of that active in liquid form and free of solvents, directly on the mat surface, whereupon it sinks promptly into the mat surface. In contrast, transfluthrin similarly deposited on a conventional, cellulosic mat sinks into the mat so slowly as to be impractical for mass production of dosed mats. Consequently, for conventional mats, the transfluthrin must be dissolved in a solvent to aid liquid migration before such mats can be dosed.

The method of the invention for delivering a volatile material from a dispensing device that uses a heat source to promote release of volatile materials from a wick designed to deliver a volatile liquid from a reservoir to a heated location within a heater wherein the volatile liquid can be heated and volatilized, includes the following steps. First, one provides, as a replacement for a conventional wick or, alternatively, for both a conventional wick and reservoir, a substrate having granular particles adhered together to form a body. The body has a network of pores and passages, the interior surfaces of which are non-reactive and non-absorptive with respect to the volatile material to be dispensed, the body being so formed as to occupy the heated location within the heater. A volatile material is disposed in the pores. The substrate is placed within the dispensing device in the space normally occupied by a wick. Then the volatile dispensing device is activated to release the volatile material from the pores, which volatile material is then dispensed.

In another aspect of the invention, a method is provided for dispensing a volatile material from a heating device having (a) an enclosed heating chamber designed to hold the a volatile-impregnated substrate therewithin, the heating chamber having chamber walls and being vented to the outside air; (b) a fuel burner; and (c) an air flow path to guide hot gases generated by the fuel burner past the substrate to heat the substrate and release the volatile material therefrom. The method includes the steps of first providing a substrate holdable by the enclosed heating chamber, the substrate having granular particles adhered together to form a body having a network of pores and passages, the interior surfaces of which are non-reactive and non-absorptive with respect to the volatile material to be dispensed, the substrate also having the volatile material to be dispensed, disposed in the pores. The substrate is then installed in the heating chamber, and the fuel burner is activated to release the volatile material from the pores, which volatile material is then dispensed. In an example embodiment of this aspect of the invention, the volatile material is a substance that is non-liquid at a temperature of 30° C. or below, such as transfluthrin.

In yet another aspect of the invention, a method is provided for dispensing a volatile material from a dispensing device that uses a heat source to promote release of volatile materials from a substrate by application of heat from a heating surface. The method includes the steps of first providing a substrate of a size and shape selected to fit onto the heating surface, the substrate having granular particles adhered together to form a body having a network of pores and passages, the interior surfaces of which are non-reactive and non-absorptive with respect to the volatile material to be dispensed. The substrate also has the volatile material to be dispensed, disposed in the pores. Then the substrate is installed on the heating surface, and the dispensing device is activated to cause the heating surface to heat to release the volatile material from the pores, which volatile material is then dispensed. In an example embodiment of this aspect of the invention, the volatile material is a substance that is non-liquid at a temperature of 30° C. or below, such as transfluthrin.

In still another aspect of the invention, there is provided a method for delivering a volatile material from a dispensing device that uses a heat source to promote release of volatile materials from a wick designed to deliver a volatile liquid from a reservoir to a heated location within a heater wherein the volatile liquid can be heated and volatilized. First, one provides, as a volatile material in the liquid in the reservoir, an insect control active ingredient selected from the group consisting of natural pyrethrins, pyrethrum extract, synthetic pyrethroids, and mixtures thereof. Then, one provides, as a wick, a substrate comprising granular particles adhered together to form a body having a network of pores and passages. The interior surfaces of the substrate are non-reactive and non-absorptive with respect to the volatile material to be dispensed. The body is formed to occupy the heated location within the heater, and activation of the heat source of the volatile dispensing device releases the volatile material from the pores to dispense the volatile material. The construction of the substrate serves to limit clogging of the pores by the pyrethrum insecticides and/or associated waxes.

In still another aspect of the invention, a method for delivering a volatile material from a dispensing device that uses a moving air stream to promote release of volatile materials from a substrate held within the air stream includes the following steps. A substrate is provided of a size and shape selected to be held in the air stream, the substrate having granular particles adhered together to form a body having a network of pores and passages, the interior surfaces of which are non-reactive and non-absorptive with respect to the volatile material to be dispensed, the volatile material to be dispensed being disposed in the pores. The substrate is installed in the air stream, and the dispensing device is activated to direct the air stream to the substrate to release the volatile material from the pores, which volatile material is then dispensed. When the volatile material is an insect control active material it is preferred that the insect control active material be dispensed at an insect controlling rate until no more than 10% or even 5% residual volatile material remains in the pores, and that dispensing proceed at a substantially linear manner.

BRIEF DESCRIPTION OF THE DRAWINGS

These and other features, aspects, and advantages of the present invention will become better understood upon consideration of the following detailed description, appended claims, and drawings where:

Like reference numerals will be used to refer to like or similar parts from Figure to Figure in the following description of the drawings.

DETAILED DESCRIPTION OF THE INVENTION

Figure 1A:
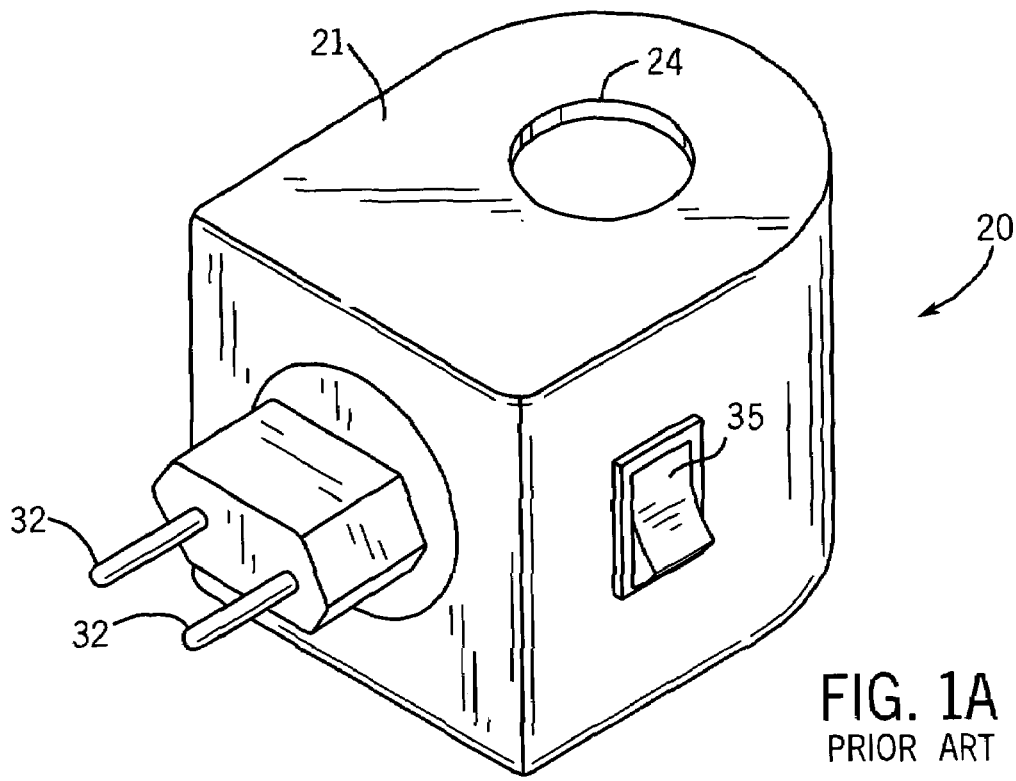
FIG. 1A is a perspective view showing a prior art device for dispensing volatile materials from a wick according to the invention.
Figure 1B:
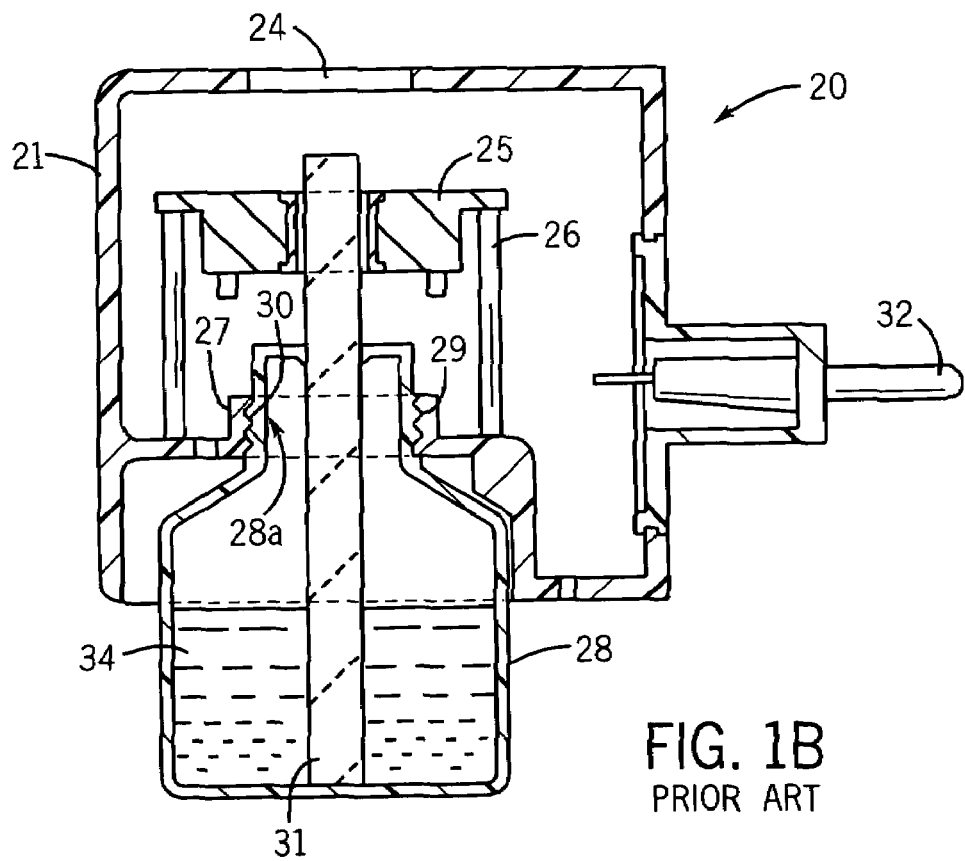
FIG. 1B is a side cross-sectional view of the device of FIG. 1A.

Referring to FIGS. 1A and 1B, there is shown a prior art heated volatile dispensing device 20 in which a heat source is used to promote the wicking action and release of a volatile material from a wick immersed in a volatile liquid contained in a reservoir. The dispensing device 20 includes a body 21 having a vapor outlet 24 formed in the center of the top of the body 21. A ring heater 25 having an opening extending vertically there through is provided inside the body 21 below the vapor outlet 24. The ring heater 25 is supported by a stay 26. Provided under the heater 25 is a bottle socket 27 having an opening extending vertically there through. The socket 27 is formed on its inner periphery with a threaded portion 30 adapted for threaded engagement with a threaded portion 29 on the outer periphery of the mouth 28a of a volatile liquid bottle 28.

As shown in FIG. 1B, the bottle 28 is provided with a wick 31 that is insertable into the ring heater 25 concentrically therewith when the bottle 28 is threaded at its mouth 28a into the socket 27. The wick 31 is immersed in the liquid 34 in the bottle 28 and upwardly transports the liquid 34 contained in the bottle 28 by capillary action. The wick 31 is typically formed from a fired porous ceramic or a sintered plastic material.

Electrical plug blades 32 in a pair are fixed to the body 21 on its rear side. The plug blades 32 are connected to the ring heater 25 in the usual manner using electrical connections.

The ring heater 25 is energized by inserting the plug blades 32 into an electrical outlet and activating switch 35 whereby the ring heater 25 produces heat to heat the upper portion of the wick 31. The heat may promote upward transport of the liquid 34 in the wick 31. The liquid chemical 34 in the wick 31 is vaporized by the heat from the ring heater 25. A more detailed description of this type of device can be found in U.S. Pat. No. 5,290,546.

The wick 31 may be simply made of the substrate of the invention, whereupon even solutions containing natural pyrethrums can be delivered by the wick without the wick clogging, even over as much as forty-five, sixty, or more eight-hour nights, which are typical use expectations for insect control products delivering insect control actives via a wick to a heater. Such a wick 31 may be cylindrical or any other convenient shape.

Figure 2:
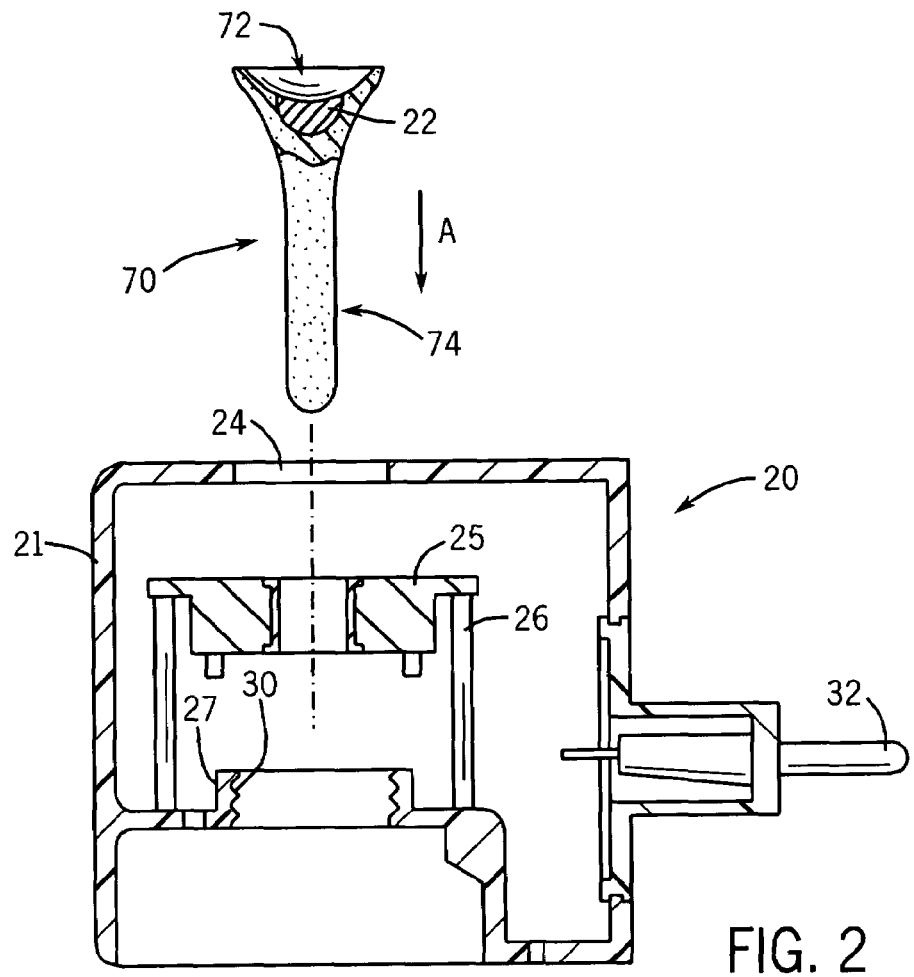
FIG. 2 is a side cross-sectional view of an embodiment of a wick according to the invention being placed into the dispensing device of FIGS. 1A and 1B.
Figure 3:
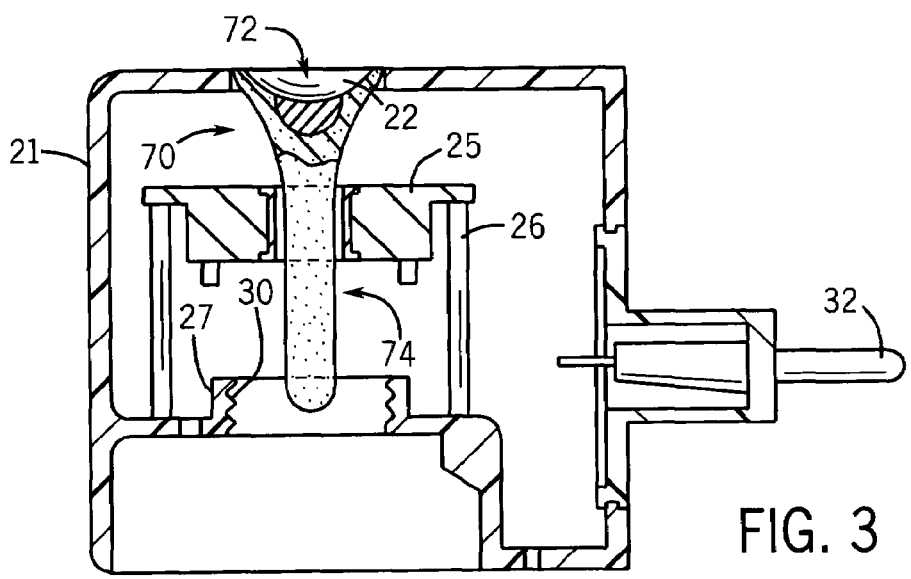
FIG. 3 is a side cross-sectional view of an embodiment of a wick according to the invention installed in the dispensing device of FIGS. 1A and 1B.

Turning now to FIGS. 2 and 3, the dispensing device 20 is shown without the bottle 28 and associated wick 31, which are replaced by a porous peg 70 according to the invention that is impregnated with a volatile material 22. The porous peg 70 includes an inverted truncated cone shaped head 72 and a cylindrical body 74 that extends downwardly from the head 72. The body 74 of the peg 70 is made small enough to be inserted from above into the hole 24 of the dispensing device 20, while the head 72 is made too wide to slip through the hole 24. The body 74 of the peg 70 is also made small enough to be insertable into the ring heater 25 concentrically therewith as shown in FIG. 3. The head 72 at the top of the peg 70 is useful for handling, allowing a user to avoid touching the volatile material 22, which is dosed only in the center (as shown in the cross-sectional view) or on the lower portion.

The porous peg 70 is inserted into the dispensing device 20 by moving the peg 70 in the direction "A" shown in FIG. 2. The ring heater 25 is then energized by inserting the plug blades 32 into an electrical outlet and activating switch 35 whereby the ring heater 25 produces heat to heat the body 74 of the peg 70. The volatile material 22 in the peg 70 is vaporized by the heat from the ring heater 25 and enters the surrounding atmosphere. The materials used for the peg 70 and the preparation of the peg 70 are described below.

Figure 4A:
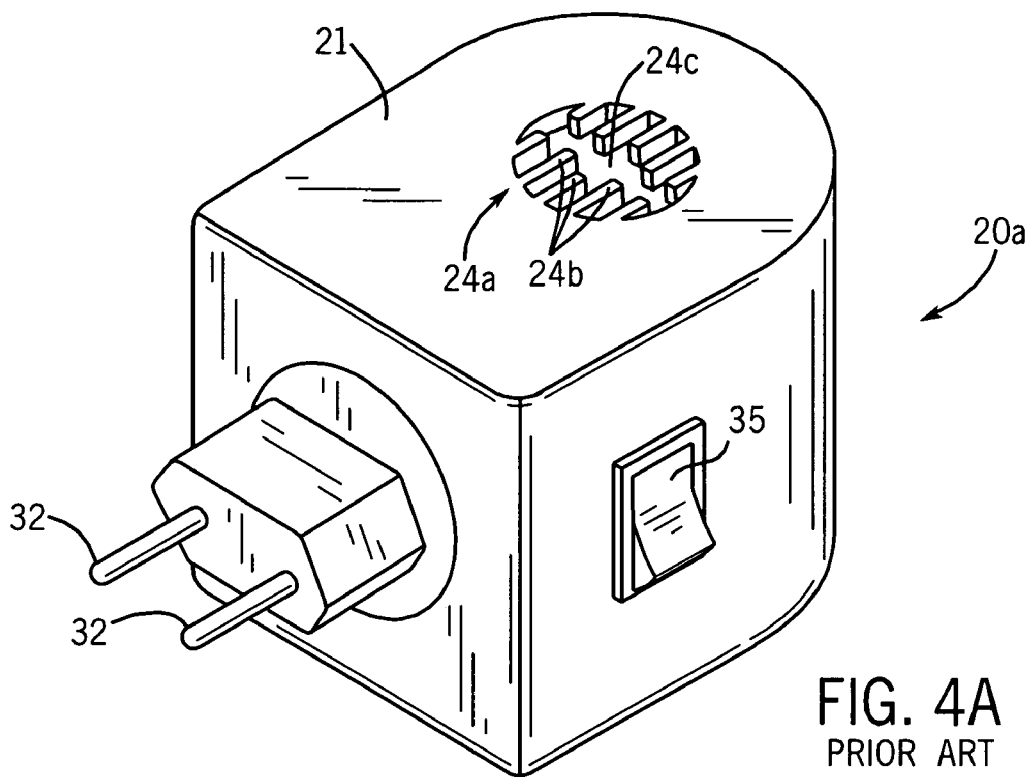
FIG. 4A is a perspective view showing another prior art device for dispensing volatile materials from another wick according to the invention.
Figure 4B:
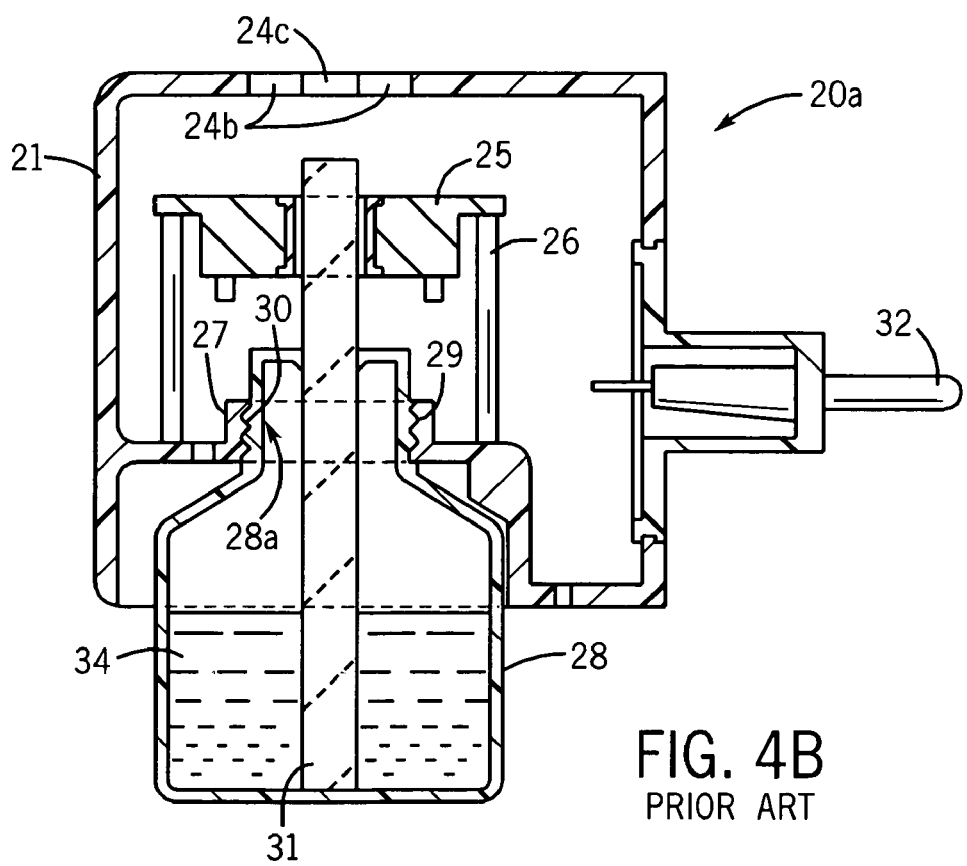
FIG. 4B is a side cross-sectional view of the device of FIG. 4A.

Referring to FIGS. 4A and 4B, there is shown another prior art heated volatile dispensing device 20a in which a heat source is used to promote the wicking action and release of a volatile material from a wick immersed in a volatile liquid contained in a reservoir. The dispensing device 20a includes a body 21 having a vapor outlet 24a formed in the center of the top of the body 21. The vapor outlet 24a includes inwardly projecting fingers 24b which define a generally rectangular opening 24c. A ring heater 25 having an opening extending vertically there through is provided inside the body 21 below the vapor outlet 24. The heater 25 is supported by a stay 26. Provided under the heater 25 is a bottle socket 27 having an opening extending vertically there through. The socket 27 is formed on its inner periphery with a threaded portion 30 adapted for threaded engagement with a threaded portion 29 on the outer periphery of the mouth 28a of a volatile liquid bottle 28.

As shown in FIG. 4B, the bottle 28 is provided with a wick 31 which is insertable into the ring heater 25 concentrically therewith when the bottle 28 is threaded at its mouth 28a into the socket 27. The wick 31 upwardly transports a liquid 34 contained in the bottle 28 by capillary action. The wick 31 is typically formed from a fired, porous ceramic or a sintered plastic material.

Electrical plug blades 32 in a pair are fixed to the body 21 on its rear side. The plug blades 32 are connected to the ring heater 25 in the usual manner using electrical connections.

The ring heater 25 is energized by inserting the plug blades 32 into an electrical outlet and activating switch 35 whereby the ring heater 25 produces heat to heat the upper portion of the wick 31. The heat may promote upward transport of the liquid 34 in the wick 31. The liquid chemical in the wick 31 is vaporized by the heat from the ring heater 25. A more detailed description of this type of device can be found in U.S. Pat. No. 5,290,546.

Figure 5:
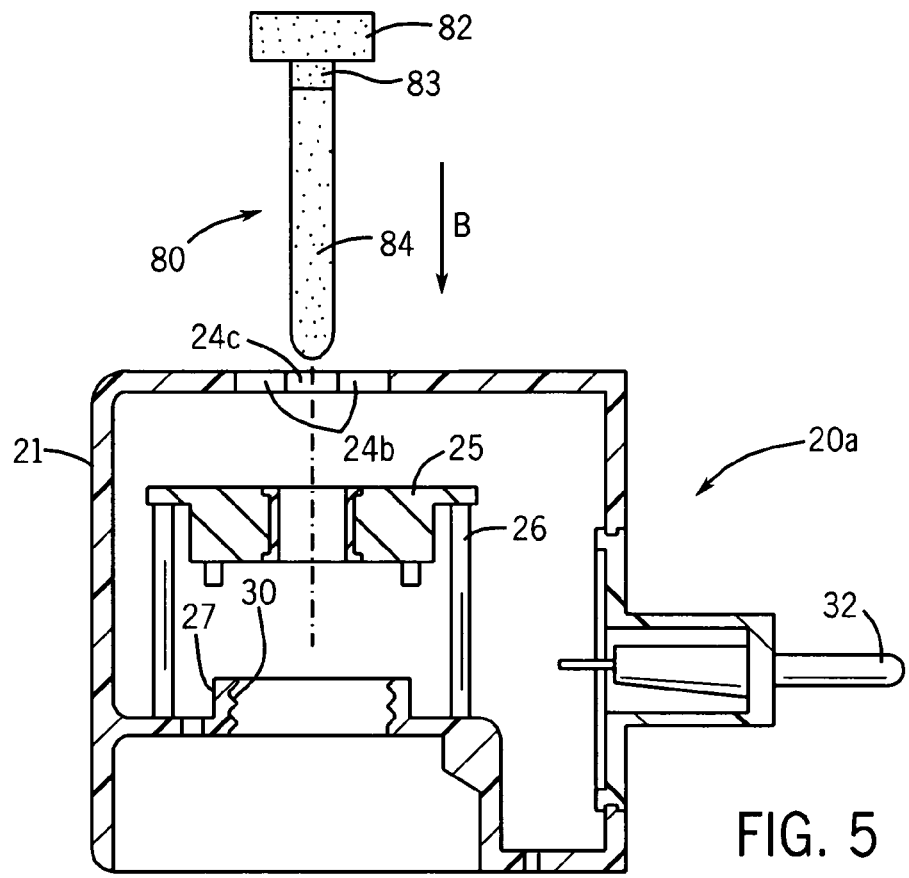
FIG. 5 is a side cross-sectional view of another embodiment of another wick according to the invention being placed into the dispensing device of FIGS. 4A and 4B.
Figure 6:
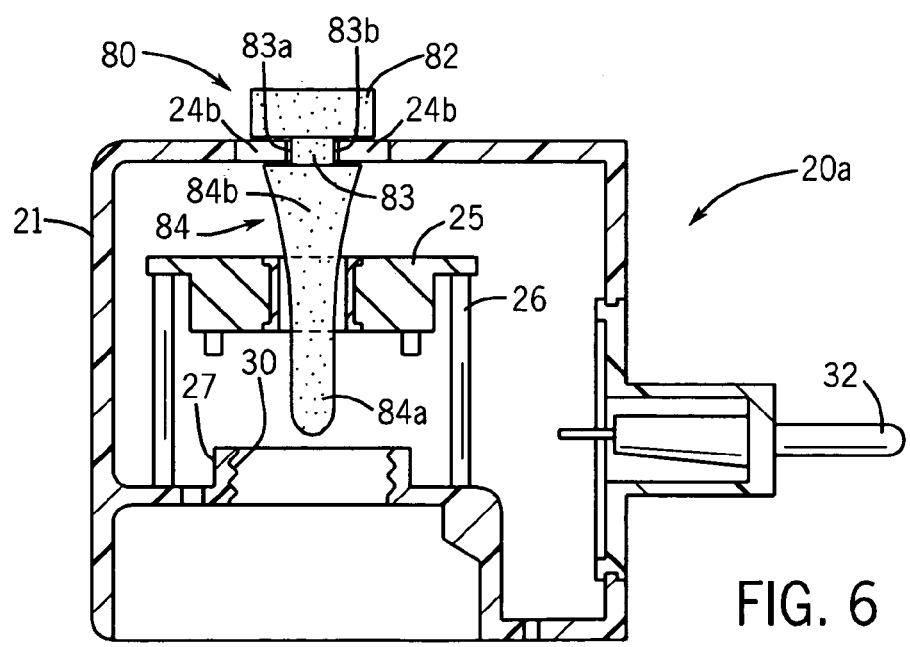
FIG. 6 is a side cross-sectional view of another embodiment of a wick according to the invention installed in the dispensing device of FIGS. 4A and 4B.

Turning now to FIGS. 5 and 6, the dispensing device 20a is shown without the bottle 28 and associated wick 31, which are replaced by another embodiment of a porous peg 80 according to the invention that is impregnated with a volatile material. The porous peg 80 includes a disk shaped head 82 and a body 84 that extends downwardly from the head 82. The body 84 of the peg 80 is shown in a side view in FIG. 5. It can be seen that in a side view, the perimeter of the body 84 of the peg 80 has an essentially rectangular shape. The body 84 of the peg 80 is shown in a front view in FIG. 6. It can be seen that in a front view, the body 84 of the peg 80 includes a lower section 84a having an essentially rectangular perimeter, a middle section 84b having an essentially V-shaped perimeter, and an upper section 83 that extends from the middle section 84b to the head 82. With the peg 84 oriented as shown in FIG. 5, the body 84 of the peg 80 is narrow enough to be inserted from above into the rectangular opening 24c of the dispensing device 20a, while the head 82 is made too wide to slip through the rectangular opening 24c. The body 84 of the peg 80 is also made small enough to be insertable into the ring heater 25 concentrically therewith as shown in FIG. 6.

The porous peg 80 is inserted into the dispensing device 20a by moving the peg 80 in the direction "B" shown in FIG. 5. The porous peg 80 may then be rotated 90 degrees into a position as shown in FIG. 6. When the peg 80 is in this position, the inwardly projecting fingers 24b of the vapor outlet 24a are positioned in grooves 83a and 83b between the middle section 84b and the head 82 of the peg 80. The peg 80 is thereby secured in the dispensing device 20a until the peg is rotated 90 and lifted up and out of the dispensing device 20a. Thus, the squared-off shank section of the shape shown fits into the existing, rectangular opening 24c in the top of the heater, entering only when turned to the correct position. Once in place, the peg can be turned, preventing its removal until turned again to its original position. After the peg 80 is inserted, the ring heater 25 is then energized by inserting the plug blades 32 into an electrical outlet and activating switch 35 whereby the ring heater 25 produces heat to heat the body 84 of the peg 80. The volatile material in the peg 80 is then vaporized by the heat from the ring heater 25 and enters the surrounding atmosphere. The materials used for the peg 80 and the preparation of the peg 80 are described below.

Figure 7:
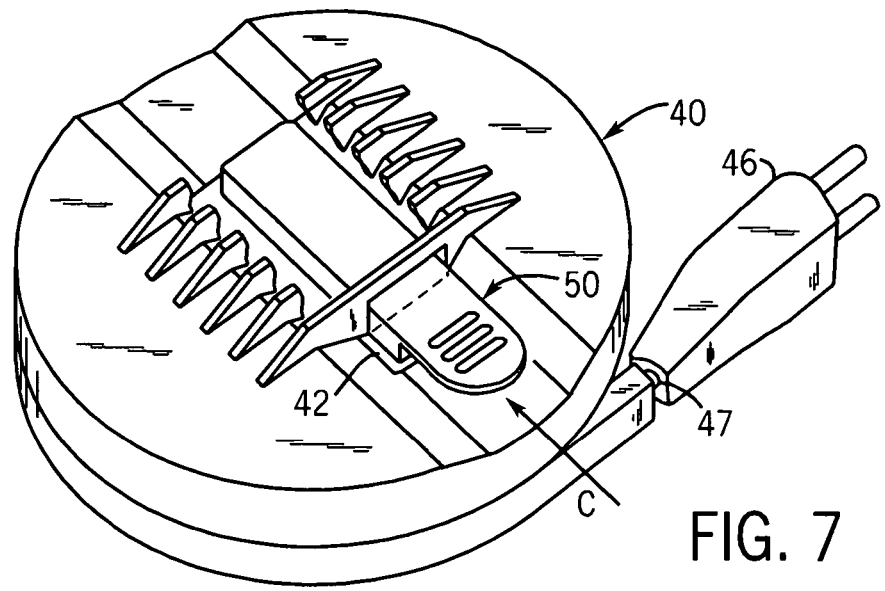
FIG. 7 is a top, perspective view showing a prior art device for dispensing volatile materials from a porous mat according to the invention.

Turning now to FIG. 7, there is shown a prior art volatile material dispensing device in which a solid porous mat impregnated with a volatile material is heated to release the volatile material. In FIG. 7, there is shown an electrical heater, indicating generally at 40. The heater is the "FUYI VAPE" heater previously described, except that the mat previously used with that heater has been replaced with a mat 50 of the present invention. The heater 40 is an electrical resistance heater, and has a flat, upwardly exposed heating plate 42 on which is placed a mat 50 of the present invention. An electrical plug 46 supplies electricity to the heating plate 42 by means of an electrical cord 47. The heating plate 42 is energized by inserting the plug 46 into an electrical outlet whereby the heating plate 42 produces heat to heat the mat 50. The volatile material is vaporized by the heat from the heating plate 42. The heating plate may be a ceramic or metal plate. This type of device is described in more detail in U.S. Pat. No. 6,031,967.

Figure 8:
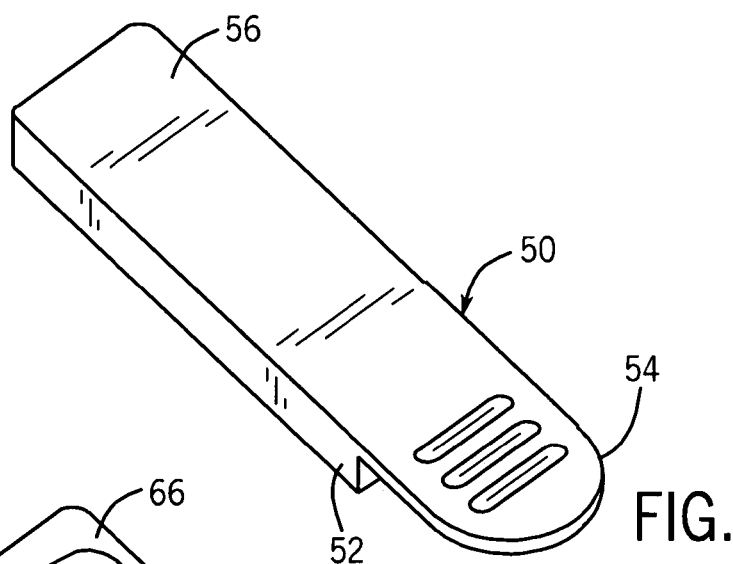
FIG. 8 is a top perspective view of a porous mat according to the invention.

Referring now to FIG. 8, there is shown one embodiment of a mat 50 according to the invention. The mat 50 includes a body 52 and a handle 54 extending outwardly from the body 52. The mat 50 is inserted into the heater 40 by moving the mat 50 in the direction "C" shown in FIG. 7. The mat 50 then rests on the heating plate 42. The heater 40 is then energized by inserting the plug 46 into an electrical outlet whereby the heating plate 42 produces heat to heat the body 52 of the mat 50. The volatile material in the mat 50 is then vaporized by the heat from the heating plate 42 and is released from the surface 56 of the mat 50 thereby entering the surrounding atmosphere. The materials used for the mat 50 and the preparation of the mat 50 are described below.

Figure 9:
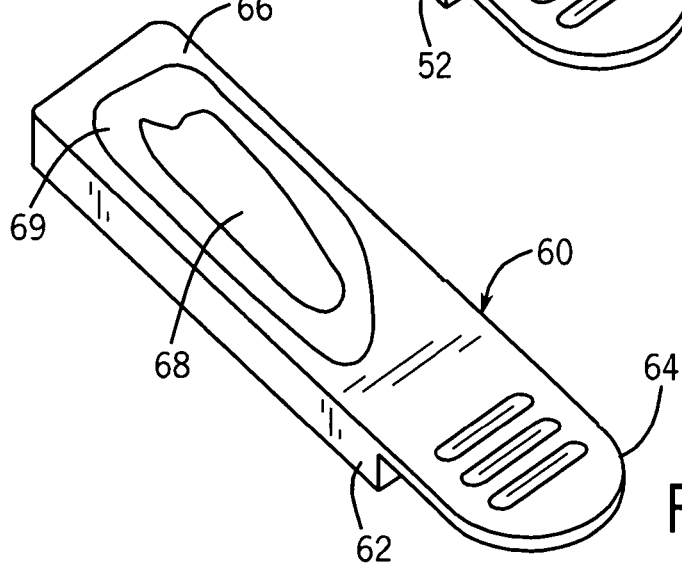
FIG. 9 is a top perspective view of another porous mat according to the invention.

Referring now to FIG. 9, there is shown another embodiment of a mat 60 according to the invention. The mat 60 includes a body 62 and a handle 64 extending outwardly from the body 62. The mat 60 is inserted into the heater 40 by moving the mat 60 in the direction "C" shown in FIG. 7. The mat 60 then rests on the heating plate 42. The heater 40 is then energized by inserting the plug 46 into an electrical outlet whereby the heating plate 42 produces heat to heat the body 62 of the mat 60. The volatile material in the mat 60 is then vaporized by the heat from the heating plate 42 and is released from the surface 66 of the mat 60 thereby entering the surrounding atmosphere.

The mat 60 differs from the mat 50 in that the mat 60 has a first region 68 impregnated with a first volatile material and a second region 69 impregnated with a second volatile material. The first region 68 and the second region 69 provide the mat 60 with advantages, particularly when used in an insecticide delivery system. A typical heater as shown in FIG. 7 will have a warm up period in which the heating plate 42 ramps up to an operating temperature. By using two regions 68, 69 with two different volatile materials such as two insecticides, insecticide delivery can be tailored to the heating characteristics of the heating plate 42. For example, the insecticide in the first region 68 may be selected to rapidly evaporate at the lower temperatures of the heating plate warm up period, and the insecticide in the second region 69 may be selected to slowly evaporate at the steady operating temperature of the heating plate. As a result, the dispensing device 40 provides for an initial burst of insecticide (from the first region 68) that clears the surrounding atmosphere of insects and a steady slower release of insecticide (from the second region 69) that keeps the surrounding atmosphere free of insects. The fastest acting volatile materials can be located where the heating plate surface heats the fastest (typically the central region of the heating plate). The materials used for the mat 60 and the preparation of the mat 60 are described below.

Figure 10:
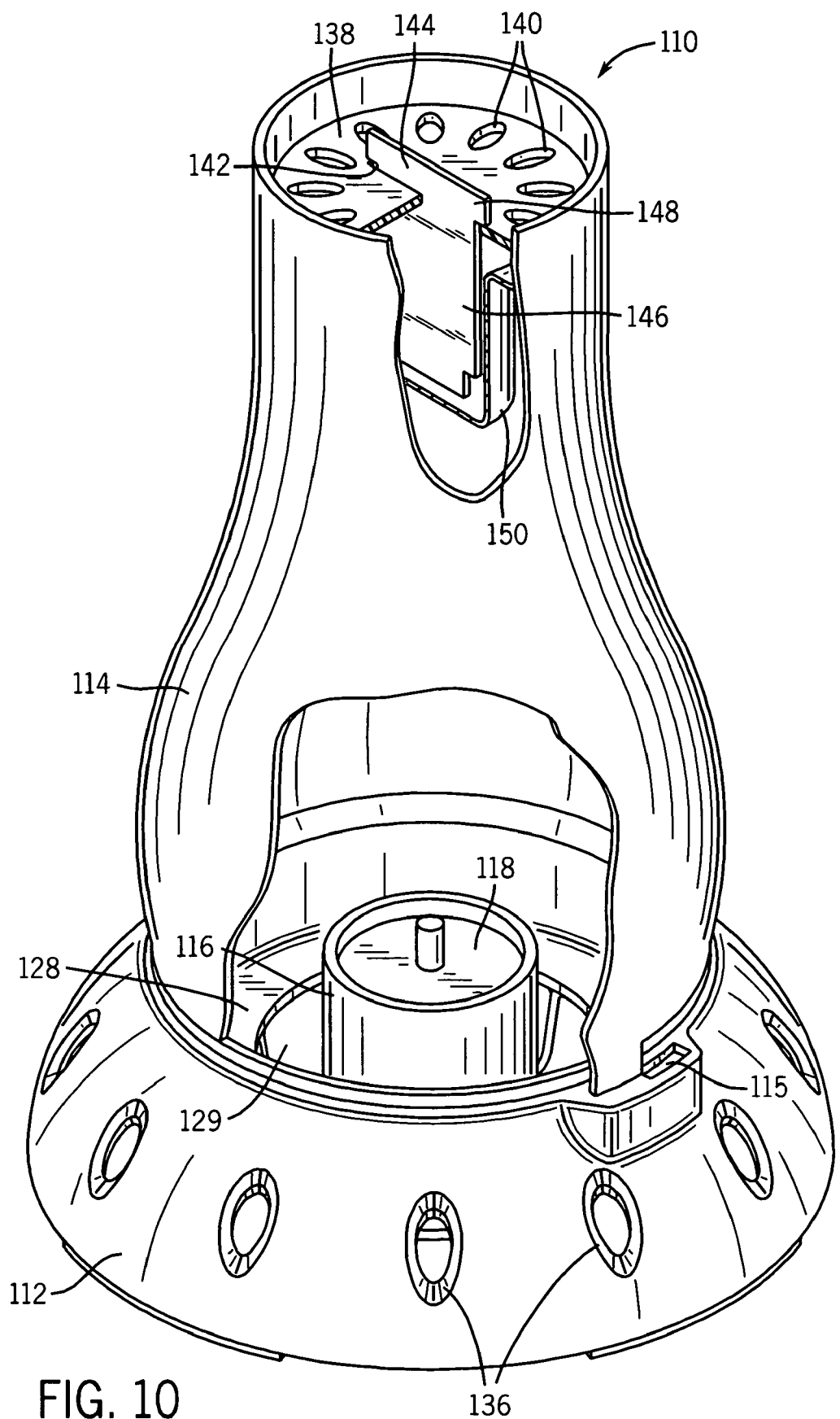
FIG. 10 is a side perspective view of another embodiment of a porous mat according to the invention installed in another prior art dispensing device.

In FIG. 10, there is shown a prior art volatile material dispensing device in which a solid porous mat according to the invention is used. The mat is impregnated with a volatile material, and is heated to release the volatile material. The dispensing device 110 has a base 112 that supports a removable chimney 114, the chimney attaching to the base 112 with locking tabs formed on the lower edge of the chimney that mate with locking slots 115 formed in the base 112. The chimney 114 can be made of a heat resistant clear or translucent plastic. The base 112 supports a candle cup 116 positioned centrally within the chimney 114. The candle cup 116 contains a wax candle. The base 112 has a base floor 128 that has a central ventilation opening 129.

A ceiling 138 is positioned within the chimney 114 at its upper end. The ceiling 138 has ceiling vents 140 and an insert slot 142 that communicate between the interior of the chimney 114 and the outside air above the chimney. Hot gases flowing upwardly from the burning candle 118 can escape the chimney 114 through the ceiling vents 140. The insert slot 142 is sized to receive a mat 144 according to the invention. The mat 144 includes a volatile bearing section 146 with laterally extending ears 148. The volatile bearing section 146 of the mat 144 is made small enough to be inserted from above into the insert slot 142, while the ears 148 are made too wide to slip through the insert slot 142. By this arrangement, the volatile bearing section 146 can be suspended within the chimney 114, with the mat 144 hanging by the ears 148. A baffle strip 150, made of a heat resistant material such as metal, is fastened to the underside of the ceiling 138. The baffle strip 150 protects the downwardly facing edge of the volatile bearing section 146 from the direct impact of the hottest gases rising from the candle. In the dispensing device 110 of FIG. 10, heating is accomplished by the direct exposure of the volatile bearing section 146 to gases from the candle. As the volatile bearing section 146 is heated by the gases, volatile material is released and is carried out of the dispensing device 110 with the escaping hot gases. This type of device is described in more detail in PCT International Patent Publication No. WO 00/78135.

Figure 11:
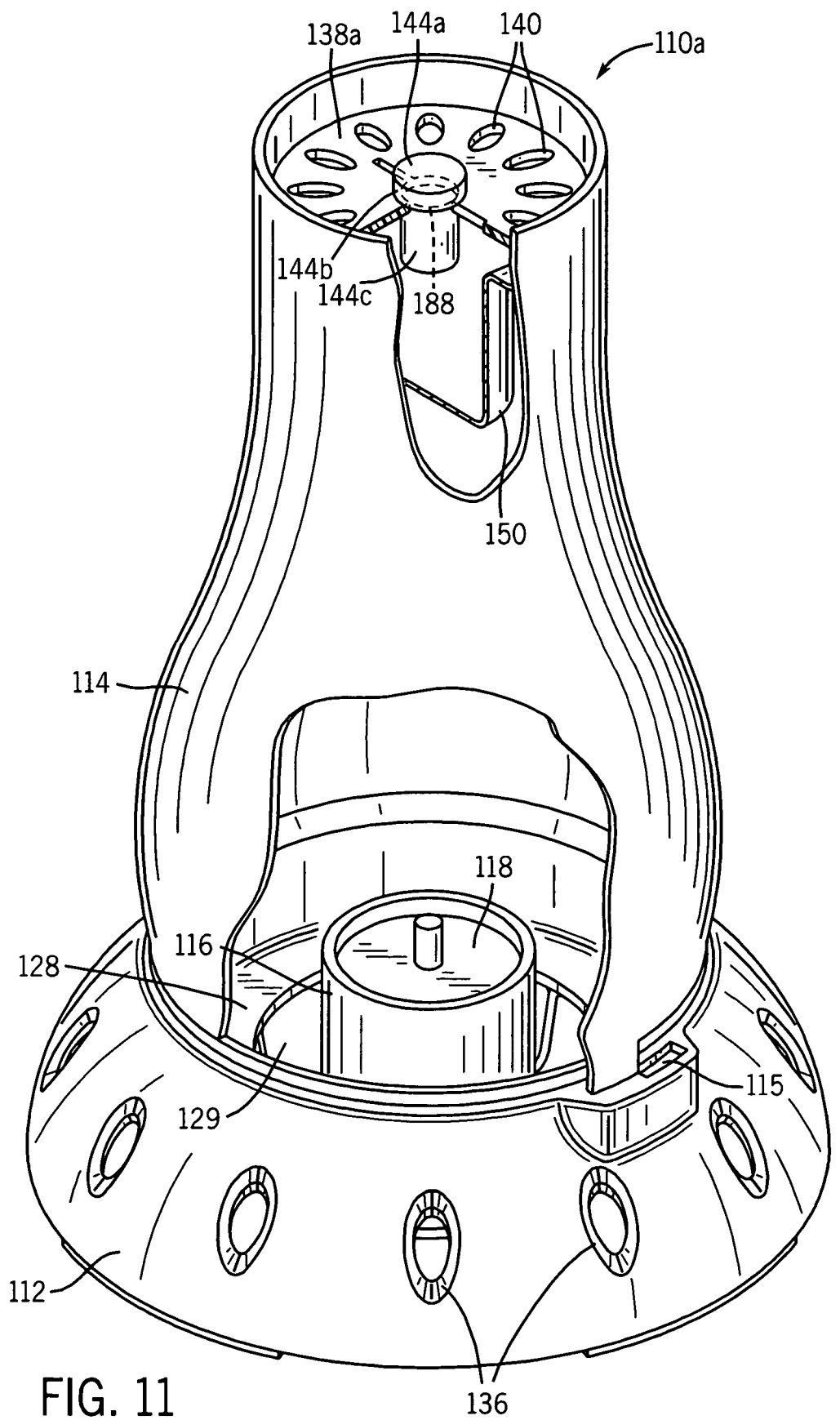
FIG. 11 is a side perspective view of an embodiment of a porous plug according to the invention installed in the prior art dispensing device shown in FIG. 10.

In FIG. 11, there is shown a prior art volatile material dispensing device 110a in which another solid porous structure according to the invention is used. The solid porous structure is impregnated with a volatile material, and is heated to release the volatile material. The volatile material dispensing device 110a of FIG. 11 has the same features as the dispensing device 110 of FIG. 10 except the mat 144 of the dispensing device 110 of FIG. 10 has been replaced by a porous plug 144a in the dispensing device 110a of FIG. 11. The porous plug 144a is installed in a circular hole 188 in the ceiling 138a of the dispensing device 110a. The porous plug 144a includes a disc shaped head 144b and a cylindrical body 144c that extends downwardly from the head 144b. The body 144c of the plug 144a is made small enough to be inserted from above into the hole 188, while the head 144b is made too wide to slip through the hole 188. By this arrangement, the porous plug 144a can be suspended within the chimney 114, with the body 144c hanging by the head 144b. In the dispensing device 110a of FIG. 11, heating is accomplished by the direct exposure of the porous plug 144a to gases from the candle. As the porous plug 144a is heated by the gases, volatile material is released and is carried out of the dispensing device 110a with the escaping hot gases. The volatile material can be applied to the lower part of the plug 144a so that a user, by handling only the head 144b (the top-most part of the plug 144a) can avoid touching any volatile material.

Having described the arrangement of the peg 70 in the dispensing device 20 of FIGS. 1A, 1B, 2 and 3, the arrangement of the peg 80 in the dispensing device 20a of FIGS. 4A, 4B, 5 and 6, the arrangement of the mats 50 and 60 in the heater 40 of FIG. 7, the arrangement of the mat 144 in the dispensing device 110 of FIG. 10, and the arrangement of the porous plug 144a in the dispensing device 110a of FIG. 11, a method for preparing the peg 70, the peg 80, the mat 50, the mat 60, the mat 144, wicks made of the substrate of the invention, and the porous plug 144a can be described.

The peg 70, the peg 80, the mat 50, the mat 60, the mat 144, wicks made of the substrate of the invention, and the porous plug 144a comprise sand particles adhered together to form a network of pores and passages. The particles are adhered together, preferably by a binder. In one example method for making the peg 70, the peg 80, the mat 50, the mat 60, the mat 144, or the porous plug 144a, individual sand particles are coated with a thin coating of the binder. The coated sand particles are then placed in a mold and compacted under elevated temperature conditions. The binder coated on the particles flows to form a thin coating on the individual particles, with the coatings fused together at their points of contact. The binder only partially fills the interstices between the particles, whereby an interconnected network of pores and passages is formed.

The sand particles may comprise silica sand particles, chromite sand particles, zircon sand particles, and mixtures thereof. Silica sand particles are typically preferred because a peg or mat formed using silica sand particles has superior fluid transport properties. Rounded particles and preferably spherical particles are the best particles because of the greater uniformity in porosity achieved and because rounded particles can be closely packed together. The best uniformity in porosity is obtained by using particles that are uniform in size.

A number of different binders can be used to adhere the sand particles together. Thermoset polymeric materials, i.e., materials that become relatively infusible upon heating, are preferred for the binder because these cross-linking polymeric materials will not flow when the formed peg or mat is heated in the dispensing device. If the binder were to flow excessively upon heating, clogging of the network of pores and passages could result. However, as used herein, the term "thermoset polymeric material" is not limited to traditional thermosetting materials but also encompasses cross linked thermoplastic materials that chemically react to become relatively infusible upon heating. The preferred binder material is a novolac resin. Other non-limiting examples of thermoset binder materials include urethane resins and highly cross linked thermoplastics such as cross linked polyethylene. Furthermore, although thermoset polymeric materials are preferred, any polymeric material can be used to bind the sand particles together, so long as the polymeric material is non-reactive and non-absorptive with respect to the volatile material to be dispensed and the polymeric material can resist the temperatures to which the substrate will be exposed in the dispensing device. Such materials will be familiar to those skilled in the art, including polymeric materials that set in response to various gas or other chemical or light treatment.

Because sand particles individually coated with the binder are flowable until adhered into a peg, mat, wick, or other shape, they may be introduced into molds of various sizes and shapes and heated to form virtually any shape structure for the peg 70, the peg 80, the mat 50, the mat 60, the mat 144, wicks made of the substrate of the invention, and the porous plug 144a. Advantageously, the sand particles may be purchased pre-coated. For example, resin coated sand particles are available from Technisand Division of Fairmount Minerals, Wedron, Ill., USA. One type of commercially available resin coated sand comprises a phenol formaldehyde novolac resin (1-6% by total weight) and a hexamethylenetetramine curing agent (<2% by total weight) coated on an aggregate including iron oxides (<15% by total weight), aluminum silicate (<15% by total weight) and silica sand (i.e., quartz). Another type of commercially available resin coated sand comprises a phenol formaldehyde novolac resin and a hexamethylenetetramine curing agent coated on chromite sand. Yet another type of commercially available resin coated sand comprises a phenol formaldehyde novolac resin and a hexamethylenetetramine curing agent coated on zircon sand.

In a most preferred embodiment, the peg 70, the peg 80, the mat 50, the mat 60, the mat 144, wicks made of the substrate of the invention, and the porous plug 144a are formed from a novolac resin coated silica sand. The novolac resin coated silica sand is low pressure injected into a heated mold at 300°

F.-700° F. to form the peg 70, the peg 80, the mat 50, the mat 60, the mat 144, wicks made of the substrate of the invention, and the porous plug 144a. The mold heat completes the irreversible cross-linking of the novolac resin. Preferably, the network of pores and passages formed occupies at least 25 to 30% by volume percent of the peg 70, the peg 80, the mat 50, the mat 60, the mat 144, or the porous plug 144a, and most preferably, the network of pores and passages formed occupies at least 40% by volume percent of the peg 70, the peg 80, the mat 50, the mat 60, the mat 144, or the porous plug 144a. Preferably, the average pore size is in the range of 20 to 200 microns, and most preferably, the average pore size is in the range of 4 to 100 microns. In one form, the substrate has different densities at different regions of the substrate.

In contrast to standard wicks used in liquid-electric volatile dispensing devices that have small pores and high tortuosity (twists and turns), the peg 70, the peg 80, the mat 50, the mat 60, the mat 144, wicks made of the substrate of the invention, and the porous plug 144a according to the invention have lower tortuosity and larger pore size while retaining adequate mass flow rate. The construction of the peg 70, the peg 80, the mat 50, the mat 60, the mat 144, wicks made of the substrate of the invention, and the porous plug 144a incorporates a polymeric binder in order to reduce the contact angle of the fluid. In addition to the polymeric binder, polymeric surface coatings such as dimethyl silicone may be applied to the surfaces of the peg 70, the peg 80, the mat 50, the mat 60, the mat 144, wicks made of the substrate of the invention, and the porous plug 144a in order to further reduce the contact angle and shield any slight imperfections and discontinuities in the peg 70, the peg 80, the mat 50, the mat 60, the mat 144, wicks made of the substrate of the invention, and the porous plug 144a from the fluid where higher contact angles could result.

A volatile material is applied to the formed peg 70, peg 80, mat 50, mat 60, mat 144, or porous plug 144a to impregnate the pores with the volatile material before the peg 70, peg 80, mat 50, mat 60, mat 144, or porous plug 144a are inserted into the dispensing device. Non-limiting examples of the thermally volatilizable materials include air scents (e.g. fragrances), pest control materials (e.g., insecticides or insect repellents), allergen control ingredients, disinfectants, and the like. Optionally, the impregnated peg 70, peg 80, mat 50, mat 60, mat 144, or porous plug 144a may be partially overmolded with plastic.

When the volatile material is an insecticide and/or insect repellent, organic phosphorous insecticides, lipidamide insecticides, natural repellents as citronella oil, natural pyrethrins and pyrethrum extract, and synthetic pyrethroids are preferred. Suitable synthetic pyrethroids are acrinathrin, allethrin as D-allethrin, Pynamin®, benfluthrin, bifenthrin, bioallethrin as Pynamin Forte®, S-bioallethrin, esbiothrin, esbiol, bisoresmethrin, cycloprothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, taufluvalinate, kadethrin, permethrin, phenothrin, prallethrin as Etoc®, resmethrin, tefluthrin, tetramethrin, tralomethrin, or transfluthrin. Other volatile insecticides as described in U.S. Pat. No. 4,439,415 can also be employed.

When a substrate of the present invention is used for the purpose of delivering fragrance, various natural and artificial perfumes may be used. Non-limiting examples of these perfumes include animal-based and plant-based natural perfumes, and artificial perfumes such as alcohols, phenols, aldehydes, ketones, terpenes, and esters.

The choice of volatile material or mixtures of volatile materials may depend on the temperatures provided by the dispensing device. For instance, the heated volatile dispensing devices 20 and 20a of FIGS. 1A and 4A typically produce a wick surface temperature of about 100° C. when used with insecticides. Therefore, the volatile material or mixture of volatile materials is selected to provide an efficient release of the volatile materials from the peg 70 or the peg 80. Likewise, the heated volatile dispensing device 40 of FIG. 7 typically produces a mat surface temperature of about 140° C. to 170° C. when used with insecticides. Therefore, the volatile material or mixture of volatile materials is selected to provide an efficient release of the volatile materials from the mat 50 or the mat 60. The heated volatile dispensing devices 100 and 110a of FIGS. 10 and 11 typically produces a mat surface temperature of about 160° C. when used with insecticides. Therefore, the volatile material or mixture of volatile materials is selected to provide an efficient release of the volatile materials from the mat 144 or the peg 144a. Other optimum temperatures are used for air care products. One advantage of a substrate according to the invention is that the substrate has heat transfer properties whereby heat may be applied at one end of the substrate and the substrate transfers heat such that the substrate has a substantially and effectively uniform temperature throughout the substrate when compared to conventional mats and wicks. Thus, a more uniform release of the volatile materials is possible from all areas of the substrate. This is not possible with conventional polymeric, fibrous, or ceramic wicks that have insulating properties (see, for example, U.S. Pat. No. 3,652,197).

As detailed above, the mat 60 of FIG. 9 has a first region 68 impregnated with a first volatile material and a second region 69 impregnated with a second volatile material. This arrangement of the first volatile material and the second volatile material is possible because of the pore structures obtainable using the sand particles and binder of the present invention. Specifically, the pore structure obtained using the sand or other non porous particles and a suitable binder provides for very controlled migration of a volatile material when the volatile material is applied to the formed mat 60. When a first volatile material is applied to the first region 68 of the mat 60, the first volatile material does not migrate into pores beyond the first region 68 of the mat 60. Likewise, when a second volatile material is applied to the second region 69 of the mat 60, the second volatile material does not migrate into pores beyond the second region 69 of the mat 60. As a result, the first volatile material and the second volatile material do not mix within the pores of the substrate. It should be noted that the mat 60 is not limited to just two regions and two volatile materials, that is, any number of regions and volatile materials is possible. The placement of different volatile materials in different regions of the mat 60 provides for tailored active materials delivery as described above with reference to faster acting and slower acting volatile materials. The use of different types of volatile materials is also possible. For example, use up indicators, such as a colored gel that co-evaporates independently of an insecticidal material, a dye in the formula that co-evaporates, and multiple volatile materials or actives (scents and insecticides), can provide an in-use cue and use-up cue.

A substrate (e.g., the peg 70, the peg 80, the mat 50, the mat 60, the mat 144, wicks made of the substrate of the invention, and the porous plug 144a) according to the invention has many advantages. For example, the sand based substrate provides fewer declines in daily delivery rates from a dispensing device, and less clogging from polymerized active materials (e.g., pyrethrum and limonene) in liquid wick applications.

Volatile material migration is less with a substrate according to the invention versus conventional paper and ceramic wicks and mats thereby allowing for precise placement of different volatile materials at different regions of the substrate. The substrate is also hotter in the center than existing paper mats which is an advantage for mat products.

An example substrate (e.g., the peg 70, the peg 80, the mat 50, the mat 60, the mat 144, wicks made of the substrate of the invention, and the porous plug 144a) according to the invention having a transfluthrin insecticide is particularly advantageous. For instance, volatile material delivery is more linear in release over a longer interval of time than other known products. This linear release can be achieved by either and both cycling on/off or running continuously, unlike other products that are not as linear no matter how they are used. Linear and super-extended volatile material delivery duration can be achieved with a miniature sized part compared to other products on the market. Higher heat conductivity and improved heat distribution allow for improved volatile release properties owing to homogeneous material porosity and a pore structure that readily conducts heat throughout and distant from the heat source. The superior thermal conductivity permits a wick to be used in conjunction with different temperature heaters or by adjusting the proximity of the wick to the heater to achieve any given desired temperature allowing for fast and slow volatile material release. The substrate readily retains pure transfluthrin in the pores resulting in less seeping or leaking, while simultaneously allowing it to completely release (no retention, no residual) when heated. Therefore, less volatile material is required to achieve the same duration of other products due to the efficiency of the system not retaining volatile material. The substrate readily absorbs pure transfluthrin into pores (quicker than ceramic or sawdust) without requiring solvents, heat, or drying, achieving the elimination of volatile organic compounds ("VOC's") emitted during the manufacturing operation. Super extension of volatile release duration can be achieved with no VOC's emitted during operation due to the elimination of solvents, performance uncommon to the industry standard that uses solvents to extend release. The substrate provides less clogging of additives that thermally degrade compared to ceramic or cellulose materials. The substrate works with liquids with a reservoir or without liquids as the reservoir.

EXAMPLES

The following Examples are presented in order to further illustrate the invention. They are not intended to limit the invention in any way.

Example 1

An insecticidal formulation suitable for impregnating the formed peg 70 or peg 80 can be prepared by mixing the following ingredients in Table 1. The formed peg 70 or peg 80 of the present invention (which is suitable for use in electrically-heated liquid vaporizers) is compatible with the formulation of Table 1 which contains 1.2% Prallethrin, 1.25% pyrethrum, 2% butylated hydroxy toluene, 0.04% limonene and the balance isoparaffin solvent. Until the present time, clogging problems in typical ceramic and sawdust wick systems did not allow utilization of this type of formula, which contains natural components like pyrethrins and terpenes.

TABLE 1

| Weight Percent of Formulation | Common name or commercial name | Chemical name | Function in the formulation |
|---|---|---|---|
| 94.36% | Isopar-V | isoparaffinic hydrocarbon | Solvent |
| 2.31% | Kenya Pyrethrum Extract, 54% | Pyrethrin Conc. 54% | Insecticide |
| 2.00% | BHT, Technical | 2,6 di-t-butyl-p-cresol | Antioxidant |
| 1.29% | ETOC (93%) | Prallethrin 93% | Insecticide |
| 0.04% | d-limonene | d-limonene | Fragrance |

Example 2

Another insecticidal formulation suitable for impregnating the formed peg 70, peg 80 or mat 50 can be prepared by using the following ingredient in Table 2. Substrates can be dosed with transfluthrin by depositing the desired amount of that active in liquid form and free of solvents, directly on the substrate surface, whereupon it sinks promptly into the surface. Transfluthrin is solid at room temperature but forms a liquid at about 32° C. Thus, liquid forms of transfluthrin can be obtained by heating solid transfluthrin to a temperature of approximately 32° C. or above. When loading a substrate according to the invention with straight transfluthrin as in this Example and heating the loaded substrate with an approximately 70° C. heater, the transfluthrin comes off in a linear manner and essentially all of the transfluthrin comes off the substrate.

TABLE 2

| Weight Percent Based on Total Weight of Peg and Formula | Common name or commercial name | Chemical name | Function within the formulation. |
|---|---|---|---|
| 5.0% | Transfluthrin | | Insecticide |

Example 3

An insecticidal formulation suitable for impregnating the formed mat 50 can be prepared by mixing the following ingredients in Table 3.

TABLE 3

| Weight Percent of Formulation | Common name or commercial name | Chemical name | Function within the formulation. |
|---|---|---|---|
| 20% | Isopar M | Isoparaffinic Hydrocarbon | Solvent |
| 40% | ETOC | Prallethrin | Insecticide |
| 40% | Piperonyl Butoxide | Piperonyl Butoxide | Insecticide |

Example 4

An insecticidal formulation suitable for impregnating the mat 144 or porous plug 144a can be prepared by mixing the following ingredients in Table 4.

TABLE 4

| Weight Percent Based on Total Weight of Peg and Formula | Common name or commercial name | Chemical name | Function within the formulation |
|---|---|---|---|
| 23.75000 | Pynamin Forte | bioallethrin | Insecticide |
| 2.73000 | Yoshinox 425 | | Stabilizer |
| 0.13000 | C.I. Solvent Blue 35 CI 61554 | | Colorant |
| 0.17000 | isopropyl myristate | | Solvent |
| 9.08000 | Isopar M | Isoparaffinic Hydrocarbon | Solvent |
| 1.15000 | ethyl alcohol | | Diluent |
| 0.50000 | Bitrex | denatonium benzoate | Bittering Agent |
| 62.49000 | Mat or Plug | | Carrier |

Example 5

A chemically-bonded sand wick was prepared by molding under compaction at an elevated temperature of at least 300° F. a commercially available novolac resin coated silica sand available from Technisand Division of Fairmount Minerals, Wedron, Ill., USA. The chemically-bonded sand wick exhibited a very fast rate of imbibition relative to ceramic and sawdust types of absorbent wicks used in conventional heated liquid electric dispensing devices. Electron micrographs showed a difference in pore size between the typical ceramic or sawdust wick and the chemically-bonded sand wick of the invention. When impregnated with the formula of Example 1, sawdust wicks in vaporizers showed a decline in delivery rate for the formula of Example 1 versus a control. When impregnated with the formula of Example 1, the chemically bonded sand wick of this Example showed no substantial decline in delivery rate over time for the test formula of Example 1 versus a control formula.

Thus, there has been provided improved volatile impregnated substrates, such as wicks and mats, that can be used in a dispensing device that uses active means (such as a heat source or moving air) to promote the release of the volatile material from the substrate. The invention satisfies a need for volatile impregnated substrates that provide improved efficacy, safety, cost, compatibility with existing volatile dispensing devices and environmental advantages.

In terms of improved efficacy, the volatile release rate (e.g., mg./hr.) of a substrate according to the invention is more consistent over product life (e.g., intended use periods such as 8 hours, 12 hours, 45 days, 60 days) compared to conventional wicks and mats; the release rate duration can be extended beyond the product life of conventional wicks and mats; and a more consistent release rate (e.g., mg./hr.) more tolerable of heater/candle temperature variability is possible. The substrate does not burn (volatile materials with solvents may burn out); the substrate provides gritty texture surface that is considered a deterrent against child sucking; and the volatile material can stay in center of the substrate, where placed, and migrates to heat, making possible handles that help prevent finger contact with volatile material.

In terms of cost, the substrate of the invention capitalizes on existing dispensing devices in the market; the sand based mat costs are comparable to a paper mat as many mats can be prepared in a single mold; the substrate can perform with or without the metal baffle strip 150 shown in FIGS. 10 and 11; the substrate can eliminate the need for the plastic bottle, wick, insert and solvent formula of FIGS. 1B and 4B; and the substrate can use volatiles that do not require solvents. With respect to compatibility, the substrate is conducive to cost-effective designs for existing products with new shapes & textures (i.e., new lock-in key feature) and provides a longer lasting disposable product and a non-clogging refillable product. In terms of environmental advantages, the substrate is disposable with 96% natural organic elements, and has a low volatile residual, that is, the substrate empties to near zero milligrams of volatiles versus 30-60 milligrams of volatiles for existing wicks.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

INDUSTRIAL APPLICABILITY

The invention relates to improved volatile material impregnated substrates, such as wicks and mats, that can be used in a dispensing device that uses active means (such as a heat source or moving air) to promote the release of the volatile material from the substrate. The volatilizable materials may be air scents (e.g. fragrances), pest control materials (e.g., insecticides), allergen control ingredients, disinfectants, and the like. Methods for making and using the invention are disclosed.

The invention claimed is:

1. A method for delivering a volatile material from a dispensing device that uses a heat source to promote release of volatile materials from a substrate by application of heat from a heating surface, the method comprising the steps of:
   a. providing a substrate of a size and shape selected to fit onto the heating surface, the substrate having:
      i. granular particles adhered together to form a body having a network of pores and passages, the interior surfaces of which are non-reactive and non-absorptive with respect to the volatile material to be dispensed; and
      ii. the volatile material to be dispensed, disposed in the pores;
   b. installing the substrate on the heating surface; and
   c. activating the dispensing device to cause the heating surface to heat to release the volatile material from the pores, which volatile material is then dispensed;
   wherein the volatile material is an insect control active material and the device is configured such that the volatile material can be dispensed at an insect controlling rate due to application of the heat until the amount of the volatile material remaining in the pores is no more than 10% of an amount of the volatile material present in the pores immediately prior to the activating step and wherein the volatile material is an insect control active material and the device is configured such that the volatile material can be dispensed at an insect controlling rate due to application of the heat until the amount of the volatile material remaining in the pores is no more than 10% of an amount of the volatile material present in the pores immediately prior to the activating step; and wherein the volatile material comprises an insect control active ingredient selected from the group consisting of natural pyrethrins, pyrethrum extract, synthetic pyrethroids, and mixtures thereof.

2. The method of claim 1 wherein the volatile material is transfluthrin.

3. The method of claim 1 wherein the volatile material comprises an insect control active ingredient selected from the group consisting of transfluthrin, bioallethrin, prallethrin, pyrethrum extract, and mixtures thereof.

4. The method of claim 1 wherein the volatile material is essentially free of solvents when applied to the body.

5. The method of claim 1 wherein the insect control active ingredient is released from the pores at a substantially linear rate when the volatile dispensing device releases the volatile material from the pores by heating the body.

6. The method of claim 1 wherein the body includes a keying structure that engages a portion of the dispensing device to secure the body in the dispensing device.

7. The method of claim 1 wherein the body includes a rectangular section.

8. The method of claim 1 wherein the body includes a volatile bearing section and a handle.

9. The method of claim 1 wherein the substrate includes a first volatile material disposed in the pores in a first region of the body and a second volatile material disposed in the pores in a second region of the body.

10. The method of claim 9 wherein the first volatile material vaporizes at a first temperature and the second volatile material vaporizes at a second temperature higher than the first temperature.

11. The method of claim 9 wherein the first volatile material and the second volatile material do not mix within the pores of the substrate.

12. The method of claim 1 wherein the dispenser supplies heat to a portion of the body less than the whole, and the body has heat transfer properties whereby heat applied to the portion of the body is transferred at a volatile-releasing rate to the remaining portions of the body.

13. The method of claim 1 wherein the substrate has different pore sizes and porosities at different regions of the body.

14. The method of claim 1 wherein the volatile material is released from the pores at an substantially linear rate until the action of the dispenser releases no more volatile material at an effective rate.

15. The method of claim 1 wherein the volatile material is only disposed in pores in a lower part of the body.

* * * * *

UNITED STATES PATENT AND TRADEMARK OFFICE
CERTIFICATE OF CORRECTION

PATENT NO. : 7,622,134 B2
APPLICATION NO. : 11/255479
DATED : November 24, 2009
INVENTOR(S) : Davis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1069 days.

Signed and Sealed this

Twenty-sixth Day of October, 2010

David J. Kappos
*Director of the United States Patent and Trademark Office*